United States Patent
Clifford et al.

(10) Patent No.: US 10,631,990 B2
(45) Date of Patent: Apr. 28, 2020

(54) STRUCTURES FOR TREATING PATELLO-FEMORAL OSTEOARTHRITIS

(71) Applicant: Moximed, Inc., Hayward, CA (US)

(72) Inventors: Anton G. Clifford, Mountain View, CA (US); Josef L. Friedmann, Scotts Valley, CA (US); Michael E. Landry, Austin, TX (US); David Lowe, Redwood City, CA (US); Mary O'Connell, Menlo Park, CA (US); Heber Saravia, San Francisco, CA (US)

(73) Assignee: MOXIMED, INC., Fremont, CA (US)

( * ) Notice: Subject to any disclaimer, the term of this patent is extended or adjusted under 35 U.S.C. 154(b) by 513 days.

(21) Appl. No.: 14/200,335

(22) Filed: Mar. 7, 2014

(65) Prior Publication Data

US 2014/0277444 A1   Sep. 18, 2014

Related U.S. Application Data

(60) Provisional application No. 61/788,184, filed on Mar. 15, 2013, provisional application No. 61/896,550, filed on Oct. 28, 2013.

(51) Int. Cl.
A61F 2/38 (2006.01)
A61B 17/68 (2006.01)
A61B 17/86 (2006.01)

(52) U.S. Cl.
CPC ............ *A61F 2/3886* (2013.01); *A61B 17/68* (2013.01); *A61B 17/864* (2013.01); *A61B 2017/681* (2013.01)

(58) Field of Classification Search
CPC .................. A61F 2/3886; A61F 2/3877; A61F 2002/3881; A61B 17/68; A61B 17/864; A61B 2017/681
See application file for complete search history.

(56) References Cited

U.S. PATENT DOCUMENTS

| 4,502,161 A * | 3/1985 | Wall | A61F 2/30756 |
| | | | 606/286 |
| 2013/0030542 A1* | 1/2013 | Grotz | A61B 17/0642 |
| | | | 623/20.35 |
| 2013/0090694 A1* | 4/2013 | Norris | A61F 2/30739 |
| | | | 606/281 |

* cited by examiner

*Primary Examiner* — Dinah Baria
*Assistant Examiner* — Rokhaya Diop
(74) *Attorney, Agent, or Firm* — Cermak Nakajima & McGowan LLP; Malcolm K. McGowan

(57) ABSTRACT

Implant apparatus and methods are directed toward treating conditions involving the knee joint, and the patella specifically, maintain alignment or address misalignment of a patella through a full range of motion of the knee joint Exemplary devices include an elastomeric, Y-shaped device which is secured to the femur and patella on opposite ends thereof by bone anchors. The elastomeric device can be either rotatably or non-rotatably connected to the bone anchors.

4 Claims, 16 Drawing Sheets

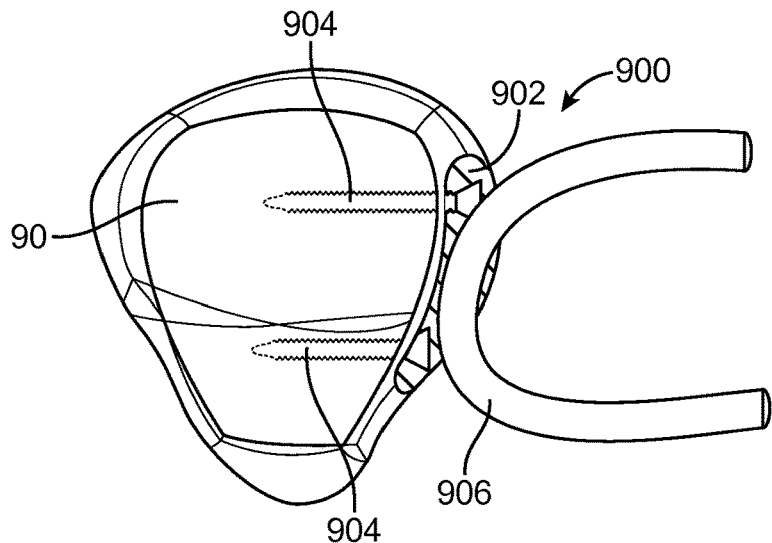
FIG. 17
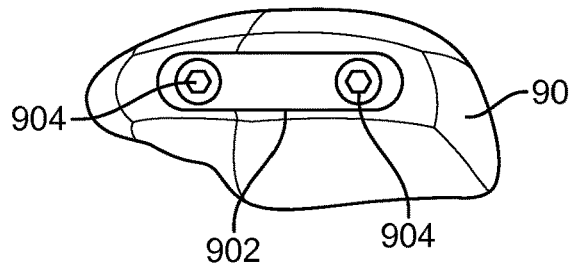
FIG. 18
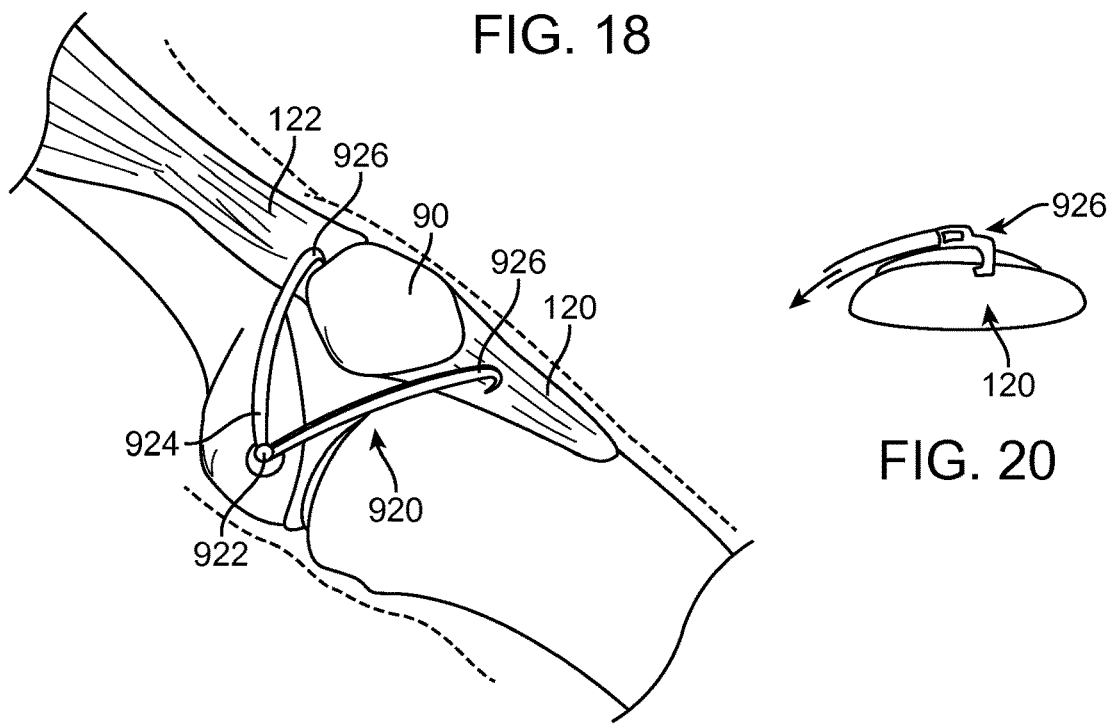
FIG. 19
FIG. 20

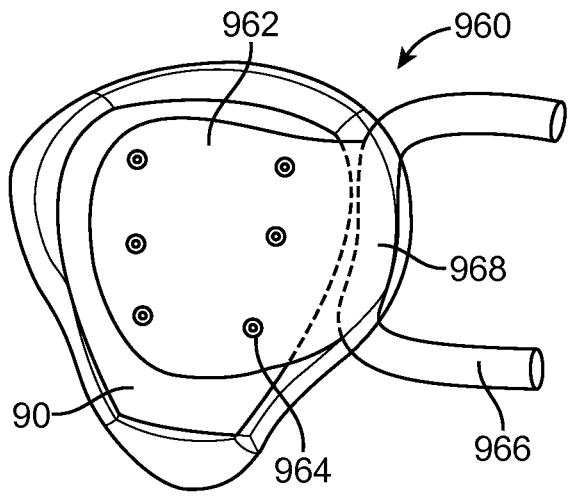
FIG. 24
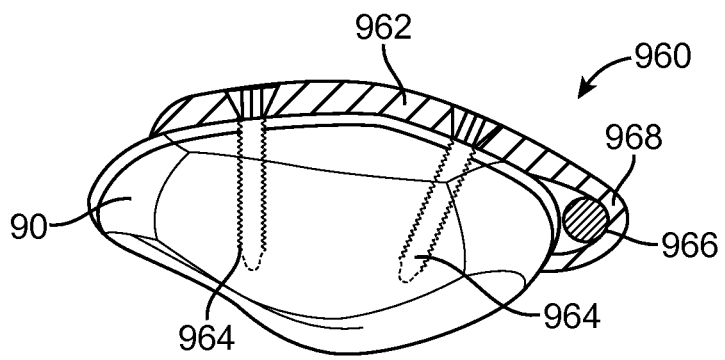
FIG. 25
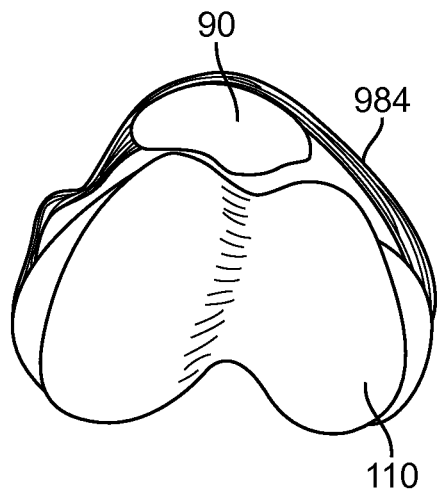 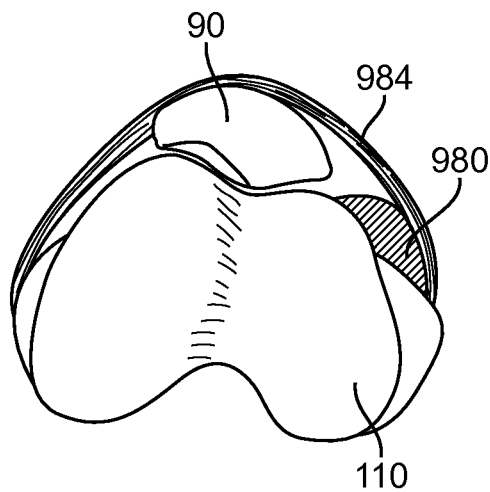
FIG. 26  FIG. 27

STRUCTURES FOR TREATING PATELLO-FEMORAL OSTEOARTHRITIS

BACKGROUND OF THE INVENTION

The present disclosure is directed towards systems and methods for treating tissue of a body and more particularly, towards approaches designed to treat a natural joint and the tracking of the patella specifically.

A joint is the location at which two or more bones make contact. They are constructed to allow movement and provide mechanical support, and are classified structurally and functionally. Structural classification is determined by how the bones connected to each other, while functional classification is determined by the degree of movement between the articulating bones. In practice, there is significant overlap between the two types of classifications.

There are three structural classifications of joints, namely fibrous or immovable joints, cartilaginous joints and synovial joints. Fibrous/Immovable bones are connected by dense connective tissue, consisting mainly of collagen. The fibrous joints are further divided into three types: sutures which are found between bones of the skull; syndesmosis which are found between long bones of the body; and gomphosis which is a joint between the root of a tooth and the sockets in the maxilla or mandible.

Cartilaginous bones are connected entirely by cartilage (also known as "synchondroses"). Cartilaginous joints allow more movement between bones than a fibrous joint but less than the highly mobile synovial joint. Synovial joints have a space between the articulating bones for synovial fluid. This classification contains joints that are the most mobile of the three, and includes the knee and shoulder. These are further classified into ball and socket joints, condyloid joints, saddle joints, hinge joints, pivot joints, and gliding joints.

Joints can also be classified functionally, by the degree of mobility they allow. Synarthrosis joints permit little or no mobility. They can be categorized by how the two bones are joined together. That is, synchondroses are joints where the two bones are connected by a piece of cartilage. Synostoses are where two bones that are initially separated eventually fuse together as a child approaches adulthood. By contrast, amphiarthrosis joints permit slight mobility. The two bone surfaces at the joint are both covered in hyaline cartilage and joined by strands of fibrocartilage. Most amphiarthrosis joints are cartilaginous.

Finally, diarthrosis joints permit a variety of movements (e.g. flexion, adduction, pronation). Only synovial joints are diarthrodial and they can be divided into six classes: 1. ball and socket—such as the shoulder or the hip and femur; 2. Hinge—such as the elbow; 3. Pivot—such as the radius and ulna; 4. condyloidal (or ellipsoidal)—such as the wrist between radius and carps, or knee; 5. Saddle—such as the joint between carpal thumbs and metacarpals; and 6. Gliding—such as between the carpals.

Synovial joints (or diarthroses, or diarthroidal joints) are the most common and most moveable type of joints in the body. As with all other joints in the body, synovial joints achieve movement at the point of contact of the articulating bones. Structural and functional differences distinguish the synovial joints from the two other types of joints in the body, with the main structural difference being the existence of a cavity between the articulating bones and the occupation of a fluid in that cavity which aids movement. The whole of a diarthrosis is contained by a ligamentous sac, the joint capsule or articular capsule. The surfaces of the two bones at the joint are covered in cartilage. The thickness of the cartilage varies with each joint, and sometimes may be of uneven thickness. Articular cartilage is multi-layered. A thin superficial layer provides a smooth surface for the two bones to slide against each other. Of all the layers, it has the highest concentration of collagen and the lowest concentration of proteoglycans, making it very resistant to shear stresses. Deeper than that is an intermediate layer, which is mechanically designed to absorb shocks and distribute the load efficiently. The deepest layer is highly calcified, and anchors the articular cartilage to the bone. In joints where the two surfaces do not fit snugly together, a meniscus or multiple folds of fibro-cartilage within the joint correct the fit, ensuring stability and the optimal distribution of load forces. The synovium is a membrane that covers all the non-cartilaginous surfaces within the joint capsule. It secretes synovial fluid into the joint, which nourishes and lubricates the articular cartilage. The synovium is separated from the capsule by a layer of cellular tissue that contains blood vessels and nerves.

Various maladies can affect the joints, one of which is arthritis. Arthritis is a group of conditions where there is damage caused to the joints of the body. Arthritis is the leading cause of disability in people over the age of 65.

There are many forms of arthritis, each of which has a different cause. Rheumatoid arthritis and psoriatic arthritis are autoimmune diseases in which the body is attacking itself. Septic arthritis is caused by joint infection. Gouty arthritis is caused by deposition of uric acid crystals in the joint that results in subsequent inflammation. The most common form of arthritis, osteoarthritis is also known as degenerative joint disease and occurs following trauma to the joint, following an infection of the joint or simply as a result of aging.

Unfortunately, all arthritides feature pain. Patterns of pain differ among the arthritides and the location. Rheumatoid arthritis is generally worse in the morning; in the early stages, patients often do not have symptoms following their morning shower.

Maladies that can affect the knee joint specifically are Patellar or kneecap pain, misalignment or dislocation. Pain can exist when there is an excess of force contact between the patella and femur. This can be due to misalignment associated arthritis or anatomical conditions specific to an individual. Kneecap dislocation occurs when the triangle-shaped patellar bone covering the knee moves or slides out of place. This problem usually occurs toward the outside of the leg and can be the result of patella misalignment due to patient specific anatomy or osteoarthritis, or from trauma.

The patella rests in the patellofemoral groove, a cavity located on the knee between the distal femur and the tibia. The sides of the patella attach to certain ligaments and tendons to stabilize and support it. The upper border of the patella attaches to the common tendon of the quadriceps muscles. The side or medial borders of the patella are attached to the vastus medialis muscle, and the lower border of the patella is connected by the patellar ligament to the tibial tuberosity. The main ligament stabilizer, the patellofemoral ligament, rests directly over the femur and the patella while the lateral and medial collateral ligaments acts as the secondary ligament stabilizers from either side of the patella.

Arthritis of the patella is one of the many causes of knee pain. Patella femoral arthritis, is identified when loss of cartilage behind the patella leads to pain in the knee. The pain typically worsens when a patient walks hills, goes up or down stairs, or does deep knee flexion. Arthritis of the patella can result from an injury to the knee joint, ordinary wear and tear, or most commonly the improper tracking of the patella on the femur when the knee does not line up properly.

Non-surgical treatments for patella femoral arthritis include pain medication and cortisone shots to help lessen the pain. However, if sufficient bone loss occurs, surgery may be necessary.

Surgical options are directed at either repair of cartilage or improvement of stability and tracking. Surgical improvement of tracking can include a lateral release where a tendon is cut to help align the patella. Other surgical options include a tibial tuberosity osteotomy, partial knee replacement and a total knee replacement, or removal of the patella entirely.

In a tibia tuberosity osteotomy, the bump on which your patellar tendon attaches (tibial tuberosity) is moved surgically by cutting the bone and adding plates and/or pins. The tibial tuberosity is moved up, down, left or right depending on the location of the damaged cartilage to move the load on the cartilage to a part of the knee that is still healthy—assuming there is such an area.

In a patellectomy the patella is removed outright. Sometimes this works, but sometimes removing the patella may hasten the onset of arthritis in the rest of the knee. A patella replacement may also be performed where part or all of the patella is replace with an implant.

Recently, less conventional approaches to treating the patella have been proposed. In one approach, a patellar implant is placed below a patellar tendon to elevate or tilt the patellar tendon. This consequently may alter patellar tracking and decrease forces on the patella to thereby alleviate pain caused by the patella contacting the femur or tibia or by decreasing force loads across the patella-femoral joint.

In a related approach, improper force distributions associated with the patella are addressed by displacing tissues in order to realign force vectors and alter movement across loading the knee joint. Here, again, an objective is to lessen the force with which the patella is pressed against the femur during the gait cycle.

Sufficient attention does not appear to have been given in prior patella treatment approaches, however, to treatment of the knee joint throughout its full range of motion. There is also a need for ensuring correct tracking of the patella on the femur.

Therefore, what is needed and heretofore lacking in prior attempts to treat joint pain associated with patella misalignment, dislocation or instability is an implantation method and implant device which addresses full range of joint movement, and which facilitates maintaining desired tracking of anatomy forming the knee joint.

The present disclosure addresses these and other needs.

SUMMARY

Briefly and in general terms, the present disclosure is directed towards treating joint structures. In one aspect, there are disclosed approaches to redistributing forces of the patella to alleviate pain or to address misalignment. A tracking pattern of the patella is assessed and steps can be taken to implant a device to correct tracking of the patella throughout a portion or a full range of motion of a knee joint or that of normal gait.

In one particular embodiment, there is provided an implant which embodies a tension cable configured to correct tracking of a patella on a femur. The implant is configured to define structure which corrects or maintains proper tracking through a full range of motion of a knee joint. The implant can also be configured to provide variable lateral or medial translation as is desired. By achieving such correction, pain associated with patella misalignment or unnatural engagement with the femur can be minimized.

In one embodiment, the implant includes a spring component and terminal ends adapted for attachment to body anatomy. One end of the implant can be affixed to a femur and the opposite end can be attached to the patella. Both or either medial and lateral corrections in patella motion throughout gait can be addressed.

In another embodiment, the implant is defined by an elastomeric material. The elastomeric material is chosen to provide desired correction to the patella during all stages of flexion. In this way, patellofemoral osteoarthritis can be treated and joint pain can be minimized.

In yet another embodiment, the implant can include tension cables or embody a combination of a spring and elastomeric material. Further, the implant can embody a rigid, pivoting structure, or a combination of each of the foregoing approaches. A system involving the contemplated implants can further include other structures that help maintain the patella in a natural trough. In this regard, a spacer can be employed under the patella tendon to help in maintaining patella positioning.

In another embodiment, a system for treating patellofemoral osteoarthritis, includes a patella tracking correction implant, the patella tracking correction implant configured to apply a variable lateral force to the patella; and a patellar tendon implant, configured to be placed below a patellar tendon.

In a further embodiment, a patella shifting implant includes a first attachment for attaching a first end of the implant to the patella; a second attachment for attaching a second end of the implant to the femur; and a tensile member extending between the first attachment and the second attachment and configured to alter a tracking pattern of the patella.

Other features and advantages of the present disclosure will become apparent from the following detailed description, taken in conjunction with the accompanying drawings, which illustrate, by way of example, the principles of the invention.

BRIEF DESCRIPTION OF THE DRAWINGS

FIG. 17 is a front view of a patella with another version of a tensioning implant;

FIG. 18 is a side view of the patella and implant of FIG. 17 without the tension member;

FIG. 19 is a perspective view of a knee joint with another version of a tensioning implant;

FIG. 20 is a side view of an attachment hook of FIG. 19 attached to a patellar tendon;

FIG. 24 is a front view of a thin plate shaped tensioning implant;

FIG. 25 is a cross sectional view of the implant of FIG. 24;

FIG. 26 is a perspective view of an improperly tracking patella;

FIG. 27 is a perspective view of the patella of FIG. 26 corrected by a tensioning implant;

DETAILED DESCRIPTION OF THE PREFERRED EMBODIMENTS

Figure 1:
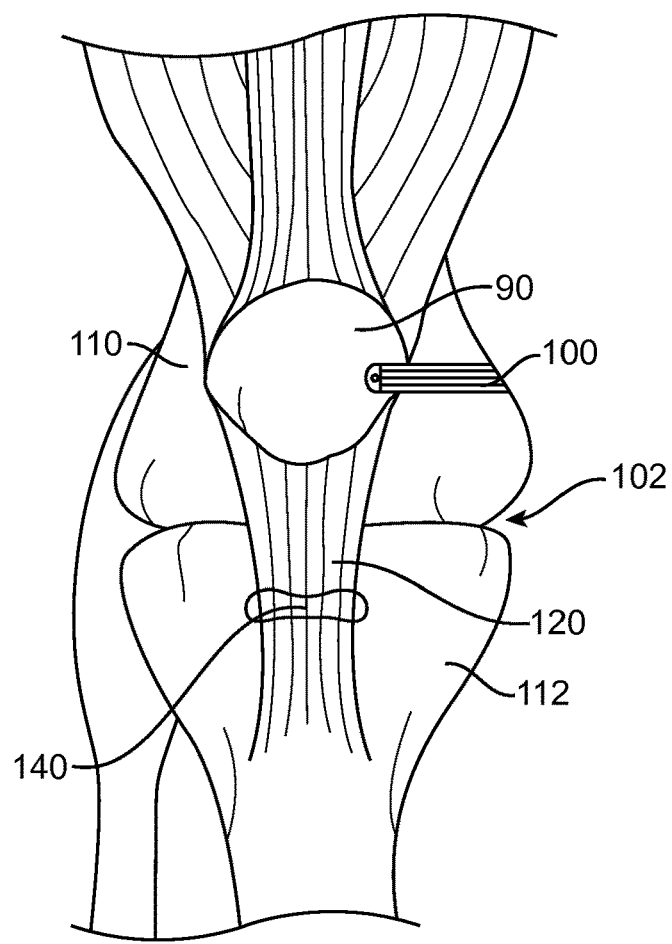
FIG. 1 is a front view, depicting an implant attached to members defining a joint.

Referring now to the drawings, which are provided by way of example and not limitation, the present disclosure is directed towards apparatus and methods for treating the knee joint, and in particular, conditions involving the patella. Patella femoral osteoarthritis can be due to natural anatomy misalignment or can be a function of an earlier injury. Significant pain can be associated with these patellar conditions and can be a direct result of excessive forces being generated between the patella and adjacent anatomy. In particular, pain results when there are undesirable force contacts between the patella and the femur. The present disclosure is directed at alleviating pain by correcting the tracking of a patella throughout the gait cycle of a knee joint.

Non-surgical treatments for patellar pain include external braces which help to keep the patella in correct alignment, sleeves that wrap around the knee below the patella to help maintain patella alignment and taping the skin around and over the patella to adjust tracking of the patella. These external methods for improving patellar tracking depend on the patient to apply the braces and tape correctly and are relatively inexact methods to improve tracking. The most common tracking problem of the patella femoral joint involves the patella being shifted too far laterally. The implants described herein are designed to provide benefits over the existing treatments by shifting the patella or rotating the patella to shift the load on the patella surfaces and reduce pain.

Figure 2:
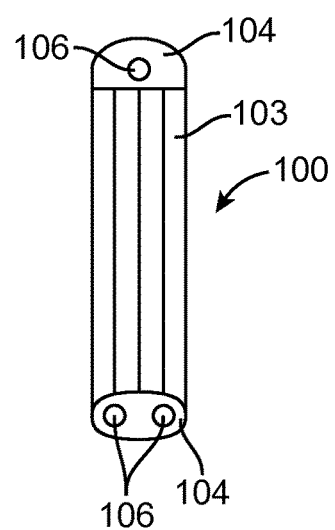
FIG. 2 is an enlarged view, depicting the implant of FIG. 1.

As shown in FIGS. 1 and 2, one approach to treating conditions involving a patella 90 can include the placement of an implant 100 at the knee joint 102. The implant 100 can embody an elongate structure including one or more tensile members 103. The tensile members 103 can having many different geometries including a cord, suture, band, strap or cable. They may be rigid in tension or elastic. In the implant of FIGS. 1 and 2, a plurality of parallel longitudinal arranged tension cables 103 are placed on the medial side of the knee joint to shift the patella medially. Terminal ends 104 of the tension cables 103 can be configured to be affixed to body anatomy. In one approach, the terminal ends 104 include through holes 106 sized and shaped to receive bone screws 108 or other affixation structures. In this way, one end of the implant 100 can be attached directly to a femur 110 of the knee joint 102 and another end can be affixed to the patella 90.

As shown in FIG. 1, the implant 100 is affixed to the tibia 112 such that the implant 100 extends laterally from the patella to the femur 110. In this way, proper tracking of the patella is achieved by applying tension to the patella in the medial direction and a reduction in pain can be achieved.

The compliance of the implant 100 is set as needed to provide the correct therapeutic force to maintain patellar tracking biased to the medial (or lateral) side. The force can be variable and can depend on a number of factors such as the initial distance between attachment locations on the femur 110 and on the patella 90. Moreover, the force can depend on the compliance of the implanted member, and the change in distance between attachment locations as the knee is flexed.

For an implant 100 on the medial side of a knee joint 102, the patello-femoral tracking and/or patello-femoral force can be altered from its native state to alleviate patello-femoral pain, OA, instability or other degeneration or disease. The same can be provided for misalignment of the patella to the medial side by lateral placement. For a patella which is improperly rotated from a desired tracking position, rotation of the patella can be achieved by changing the angle of the implant from a directly medial orientation to an angled orientation where the end of the implant attached to the femur is proximal or distal the end of the implant attached to the patella. This will allow for both medialization (lateralization) and rotation of the patella.

The implant 100 can be made of elastomer polymer, metal, ceramic and/or some combination thereof (or natural (biological) materials such as collagen, etc.) alone, or in combination, with other materials such as polymer, elastomer, and/or metal and/or ceramic. Elastomeric materials can include silicone rubber, such as Nusil MED 4840 or MED 4860, Shore A, 40 and 60, and polycarbonate-urethane alloys, such as ChronoFlex C, Shore A 80. The compliance could be achieved via material deformation (elastic) geometric deformation such as buckling or configuration change and/or compression/expansion of a fluid and/or gas such as air compressed in a piston chamber of which the length or engagement of the piston within the tube could change. The implant 100 can be configured to include structure that only applies tension during gait, and then, during only portions of the gait cycle. Such structure can also include a load absorption component acting during such intervals.

The implant 100 may be used in combination with a subpatella bar implant 140 such as one of the implants shown in U.S. patent application Ser. No. 13/708,504 which is incorporated herein by reference in its entirety. The subpatella bar implant 140 extends beneath the patellar tendon 120 and provides a redirection of the forces on the patella femoral joint.

Figure 3:
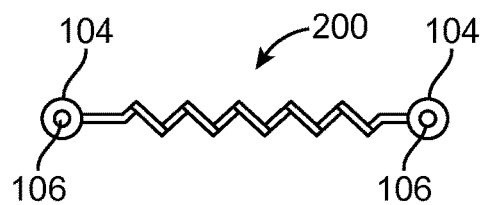
FIG. 3 is a side view, depicting an alternative approach to an implant.

As shown in FIG. 3, as stated, an implant 200 for correcting patella tracking can define an elongate member embodying a coil spring-like body. At the ends 104 of the body are structure adapted to affix the implant 200 to body anatomy. Alternative approaches to fixation can also be employed. In this regard, as before, the ends 104 can include through holes 106 for receiving bone screws or other fixation structure. The spring can be characterized by a constant force or can be configured to provide a variable correcting lateral force.

Figure 4:
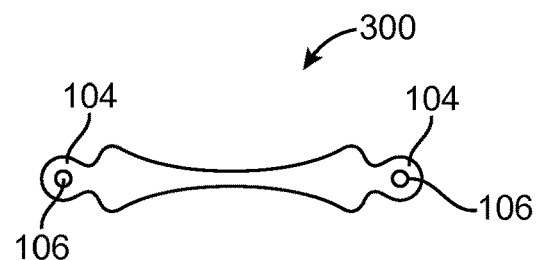
FIG. 4 is a side view, depicting yet another embodiment of an implant.

The implant 300 depicted in FIG. 4 also defines an elongate member. Here, the implant 300 embodies an elastic element with a pair of terminal ends 104 including through holes 106 for receiving anatomy fixation structures. Again, alternative approaches to fixation can be employed. Moreover, as with the spring-like implant, this implant 300 can be configured to provide a constant or variable lateral force.

Fixation of the ends of the implant can be achieved via some combination or individual application of screws directly at ends of compliant member, or by fixing bases to which suture(s), wire(s), bolts, or other similar means. Depending on fixation location, the fixation and location of the implant could be superficial or deep to existing ligamentous/tendinous/muscular structures and within or outside the patello-femoral joint capsule.

Figure 5:
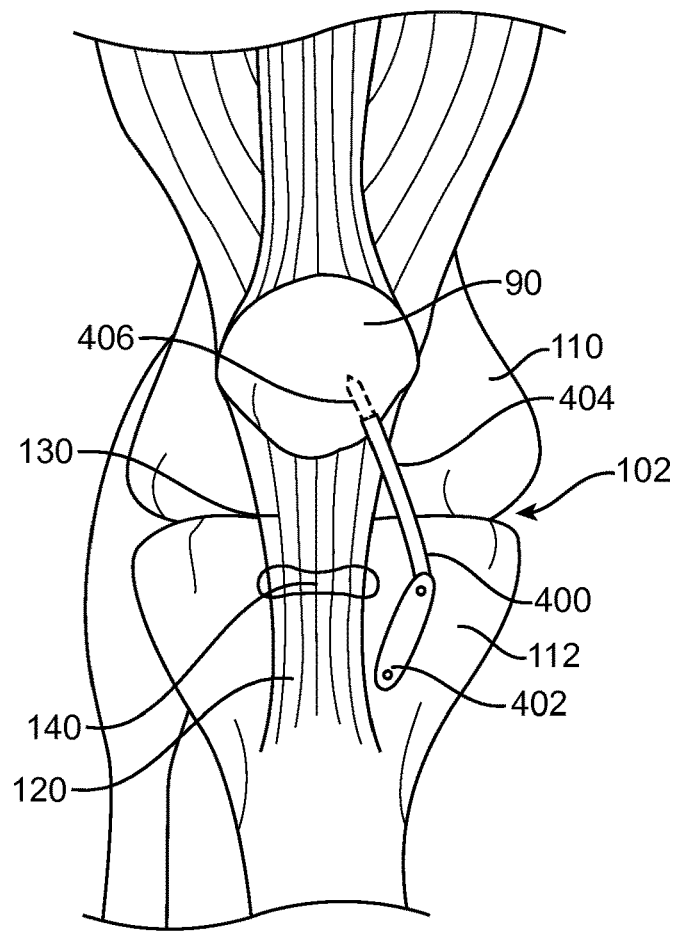
FIG. 5 is a front view, depicting another approach to an implant attached to knee anatomy.

With reference to FIG. 5, an implant 400 can further or additionally include a tibial base 402 extending from which is a cable or spring or elongate elastomeric mid-section 404. A terminal end opposite a junction between the mid-section 404 and the base 402, can be equipped with a bone screw 406. Alternatively, a patella base (not shown) can define this terminal end. As with each of the approaches and embodiments presented, a treatment system can include a subpatella bar 140 that is configured under the patella ligament to aid in unloading and/or accomplishing proper tracking of the patella 90.

Figure 5A:
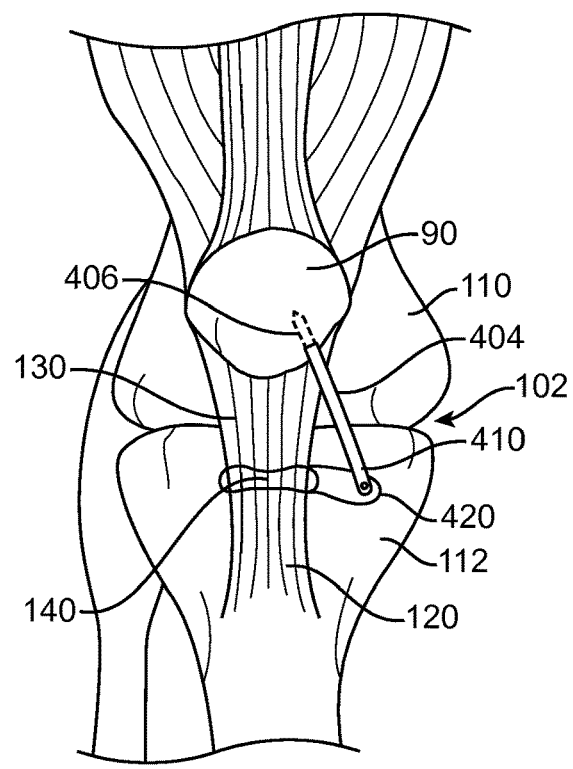
FIG. 5A is a front view, depicting another approach to an implant.

FIG. 5A illustrates an implant 410 in which the first end of the tensile member 404 is attached to the medial edge of the patella 90 and the second end of the tensile member is attached to a medially extending arm 420 of the subpatella bar implant 140 which extends medially from beneath the patellar tendon 120 and provides an attachment point for the tensile member.

Figure 6:
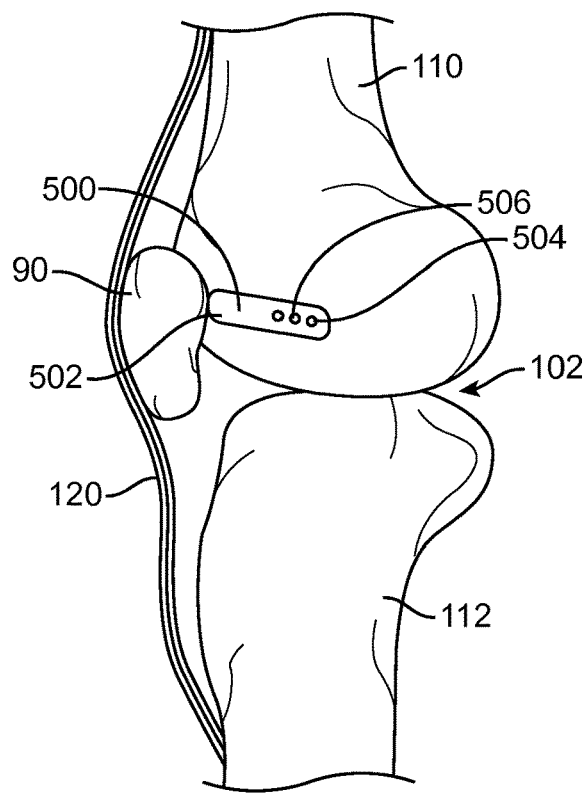
FIG. 6 is a side view, depicting a pivoting implant attached to members defining a joint.

As shown in FIG. 6, a treatment implant 500 can be embodied in a pivoting structure. A first terminal end 502 is contemplated to be affixed to the patella 90 and a second terminal end 504 is rotatably attached to the femur 110, for example. Here, the implant can define a rigid structure as well as include a force absorbing component or the previously described elastic cable or spring approaches. The device can further be made to extend below the patella 90 and have complementary structure attached to a far side of the femur. It is also contemplated that this implant can be attached to the tibia. Various attachment points 506 are also contemplated so as to provide for flexibility in implantation.

Figure 7:
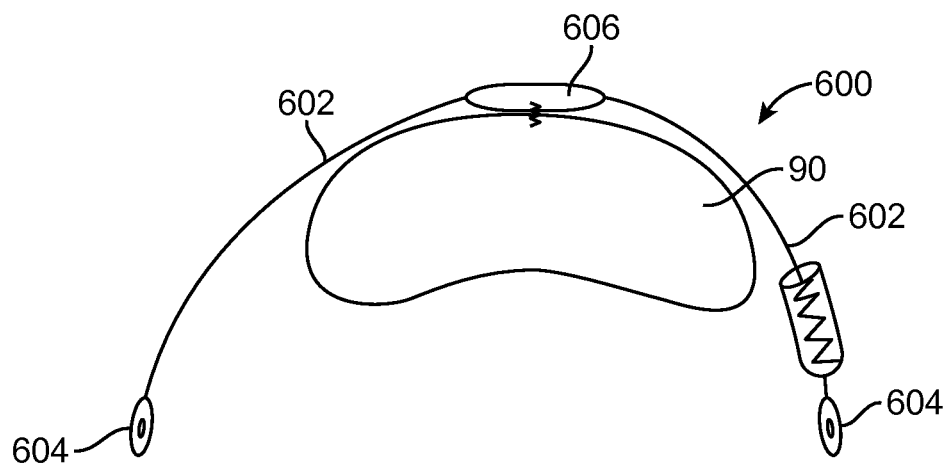
FIG. 7 is an enlarged view, depicting a bilateral implant attached to a patella.
Figure 8:
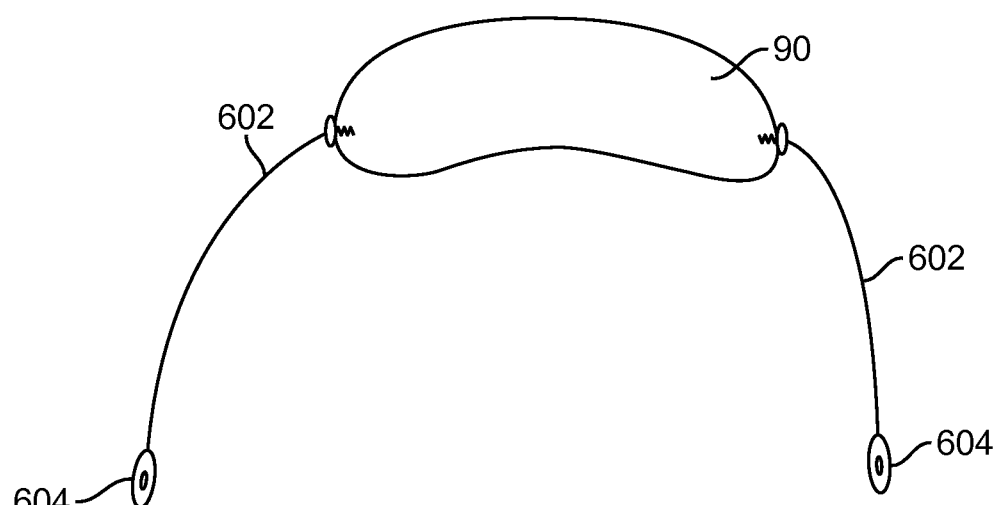
FIG. 8 is an enlarged view, depicting another embodiment of an implant attached to a patella.

Approaches to implants which have structure for bilateral attachment are shown in FIGS. 7 and 8. One implant 600 (FIG. 7) can include a pair of rigid arms 602 each of which include a terminal end 604 configured to be attached to body anatomy. A mid-section connecting structure 606 is attached to opposite ends of the rigid arms 602. This connecting structure defines a base to which the patella 90 can be attached. The arms 602 function to lift the patella 90 away from an affected or diseased area. Thus, both lifting and lateral tracking correction can be accomplished. One or more arms 602 can be further equipped with a spring or other absorber structure to provide desired unloading or lifting force to the patella. This device can be configured to provide optimal alignment of the patella 90 while also decreasing forces on the damaged cartilage between the patella 90 and the femur (not shown).

As shown in FIG. 8, as an alternative, second ends of the arms 602 can be directly attached to the patella 90. The lifting and force reduction functions are again provided with this approach. Further, the arms can in this or previous embodiments embody more elastic structure which accomplish the desired treatment. In the embodiment of FIG. 8, the arms 602 can function as leaf springs to provide a force in the direction that would lift the patella away from the femur during at least a portion of the gait cycle.

Figure 9:
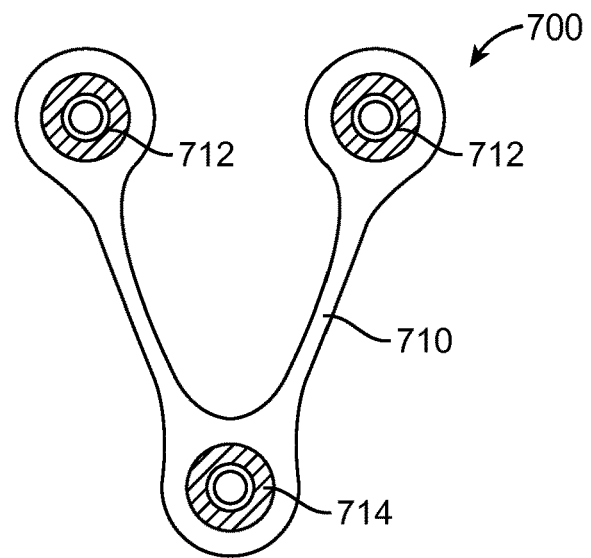
FIG. 9 is a top view, depicting another embodiment of an implant.

FIG. 9 illustrates a tensioning implant 700 including a tensile member 710 in the form of a Y-shaped elastic or elastomeric member, two patella anchors 712 and one femoral anchor 714. Although two patella anchors and one femoral anchor have been shown, other numbers of anchors may be utilized depending on the tensile forces to be achieved and the geometry of the joint. The tensile member 710 is a one piece member connected to snap lock connectors which will be described with reference to FIGS. 10 and 11. The tensile member 710 has two stretchable segments which may be of the same or different lengths. The length from the center of the patella anchors to the center of the femoral anchor is preferably about 30-60 mm. The patellar anchors 712 have diameters of about 4-6 mm, preferably about 5 mm. The femoral anchor 714 is preferably larger in diameter than the patellar anchors, about 4-8 mm, and preferably about 6 mm. The tensile member 710 may be formed of any elastomeric material such as the materials mentioned herein.

Figure 10:
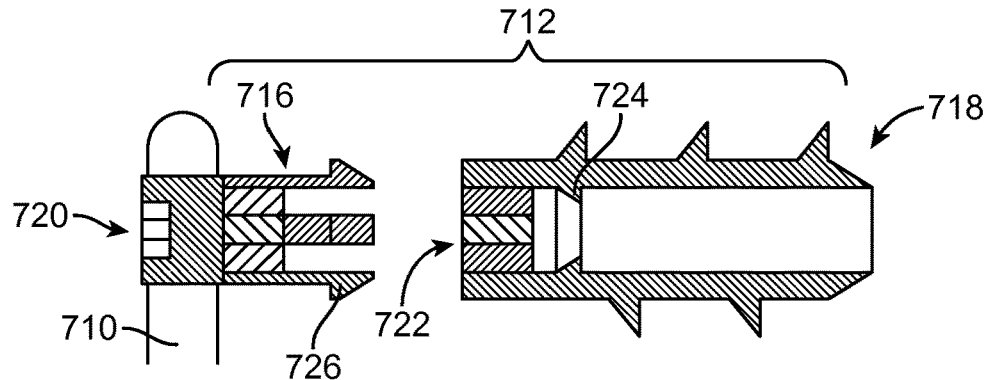
FIG. 10 is a side cross sectional view of an anchor for the implant of FIG. 9.

The patella anchor 712 shown in FIG. 10 is formed of two parts, a snap lock connector 716 and a bone anchor 718. The snap lock connector 716 is secured to the tensile member 710 and has a central hex feature 720 or other grasping feature and a plurality of snap lock prongs 726. The snap lock connector 716 has a hexagonal exterior body surface that fits into the bone anchor without rotation. The patella bone anchor 718 is a threaded anchor with a hex feature 722 for receiving both a driver and the body of the snap lock connector 716. A snap engagement feature 724 inside of the bone anchor 718 engages the snap lock prongs of the snap lock connector 716.

Figure 11:
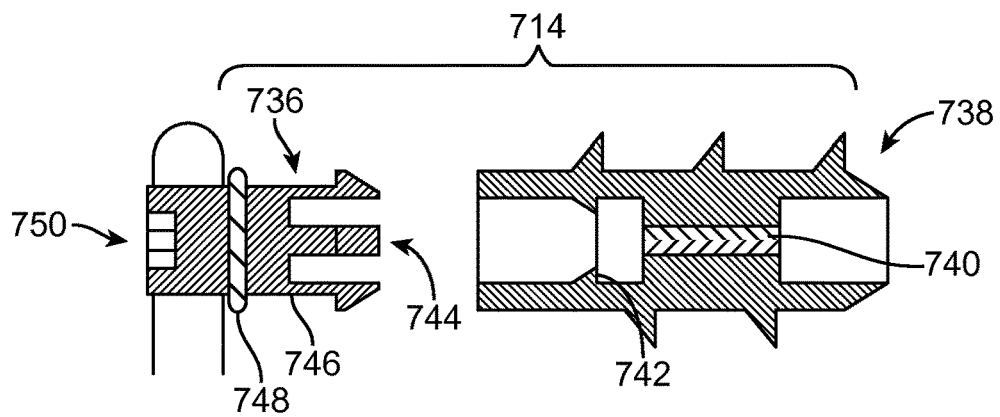
FIG. 11 is a side cross sectional view of a rotating anchor for the implant of FIG. 9.

The femoral anchor 714 shown in FIG. 11 is formed of two parts, a rotating snap lock connector 736 and a femoral bone anchor 738. As with the patella anchors 712, the femoral bone anchor 738 is a threaded anchor with an interior hex feature 740 for driving the anchor into the bone and a snap lock feature 742 for receiving prongs 744 of the snap lock connector. The snap lock connector 736 is rotatable in the femoral bone anchor to allow the tensile member 710 to rotate as the joint articulates. A pivot surface 746 and collar 748 on the snap lock connector 736 facilitate rotation of the connector in the bone anchor. A hex feature 50 or other feature of the snap lock connector facilitates grasping and inserting the snap lock connector 736 into the femoral bone anchor 738.

Figure 12:
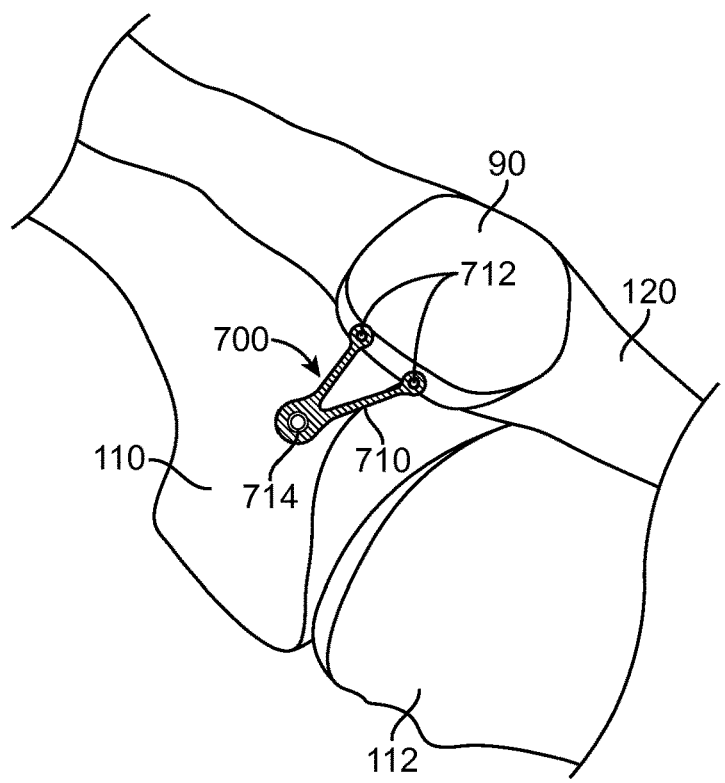
FIG. 12 is a side perspective view of the implant of FIG. 9 attached to members defining a joint.
Figure 13:
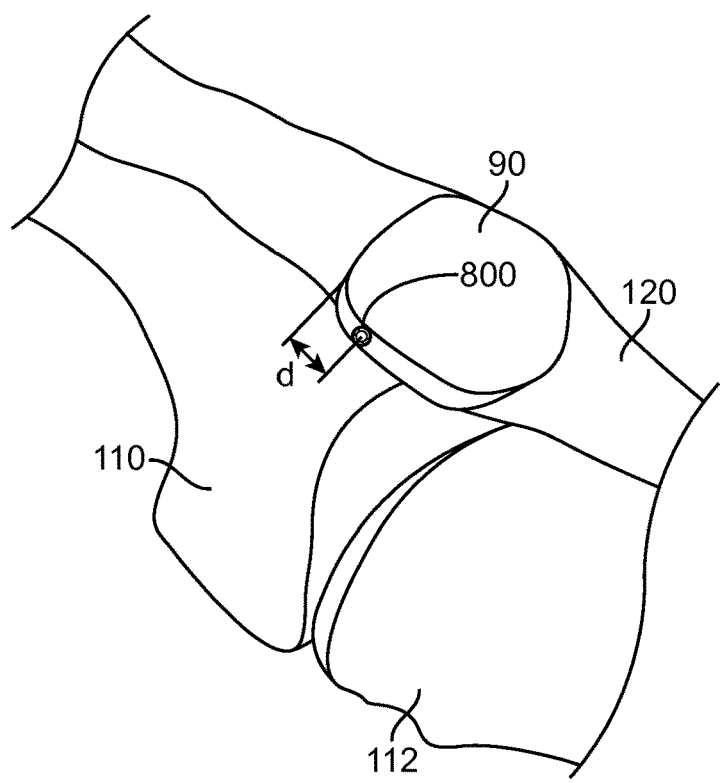
FIG. 13 is a side perspective view of the step of drilling for the implant of FIG. 9.
Figure 14:
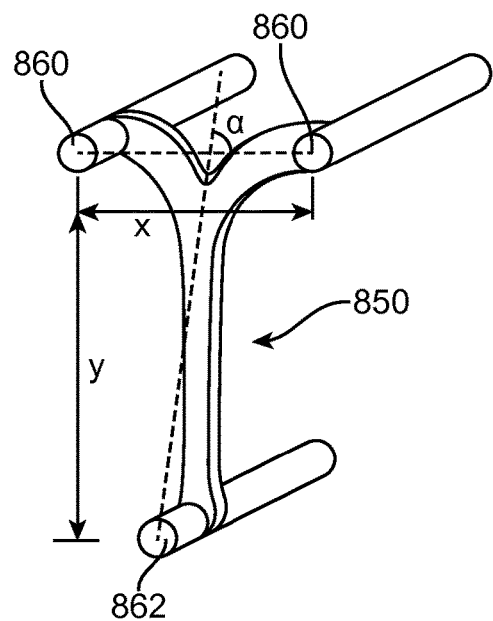
FIG. 14 is a side perspective view of a drill guide for use in implanting the implant of FIG. 9.
Figures 15, 16:
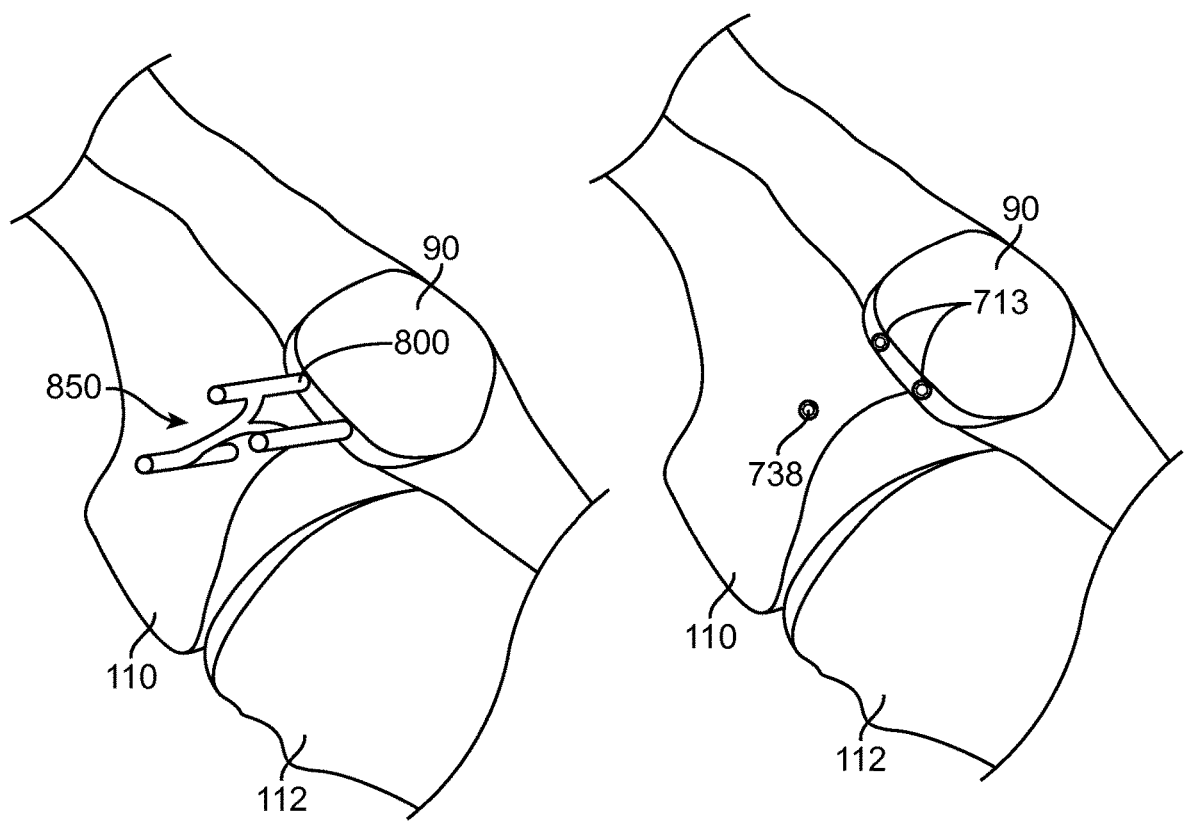
FIG. 15 is a side perspective view of the step of using the drill guide of FIG. 14.
FIG. 16 is a side perspective view of the anchors for the implant of FIG. 9 attached to members defining a joint.

FIG. 12 illustrates the tensioning implant 700 including the two tensile members 710, two patella anchors 712 and one femoral anchor 714 implanted at the medial side of a knee joint to medialize the patella. The implantation of the tensioning implant 700 according to one method includes drilling a first bind hole 800 in the patella at a distance d approximately 3-5 mm distally of the medial-proximal corner of the patella as shown in FIG. 13. A drill guide 850 shown in FIGS. 14 and 15 is then used to position the remaining two blind holes in the patella 90 and femur 110. The drill guide 850 includes two patellar guide holes 860 and one femoral guide hole 862. The angle α between the plane of the two patellar holes and the femoral guide hole 862 id dependent on the knee angle at the time of drilling. For 30-40 degrees of flexion which is the preferred implantation position, the angle α is about 70-110 degrees.

As shown in FIG. 15, the drill guide 850 is placed into an incision and onto the bone with a drill guide placed in the first blind hole 800. The second patellar guide is aligned on the medial patella and the second hole is drilled in the patella as well as the single femoral blind hole. The drill guide 850 is then removed and the bone anchors 713 and 738 are inserted into the predrilled holes as shown in FIG. 16. The tension implant 700 is secured by snapping the snap lock connectors 716 and 736 into the bone anchors 713 and 738. The knee joint is then flexed to ensure that the tension implant 700 is functioning correctly to move the patella medially, especially at high flexion angles. The incision is then sutured and the tension implant 700 remains a permanent implant. In the event that removal of the tension implant is needed one or more small incisions can be made and the bone anchors are simply removed from the bone. The implant 700 does not contact the articulating surfaces of the joint and thus the procedure is fully reversible.

FIG. 17 illustrates an alternative embodiment of a tension implant 900, including a contoured patella base 902, two or more bone screws 904 and a tension band 906. The patella base 902, as shown in a cross sectional view from an anterior of the patella in FIG. 17 and in a side view of the patella in FIG. 18 has two through bores for receiving the bone screws 904. Although two screws have been shown, other numbers of screws may be used to secure the base 902 to the patella. The screws 904 may be bicortical, unicortical or cancellous screws and can be inserted on the medial or lateral side of the patella 90 to secure the patella base 902 in place on the patella. The screws can be parallel to the coronal plane. The tension band 906 extends thought a channel in the patella base 902 and can be fixed or movable in the channel. The tension band 906 can be secured on an opposite end to the femur, tibia or fibula in a fixed or movable manner with any of the structures described herein.

FIGS. 19 and 20 illustrate another tension implant 920 which is secured to the soft tissue surrounding the patella instead of directly to the patella 90. The tension implant 920 includes a femoral fixation 922, tension bands 924 and soft tissue hooks 926. In one example, the hooks 926 are secured to the quad tendon 122 and the patellar tendon 120 above and below the patella for translation of the patella in a medial or lateral direction. For both translation and rotation, a single attachment hook distal or proximal to the patella may be employed. The soft tissue hooks may be in the form of simple hooks or looks that are secured to the soft tissue. Alternatively, each of the tension bands 924 can have a series of hooks or loops to distribute the tension forces over greater area of the soft tissue.

Figure 21:
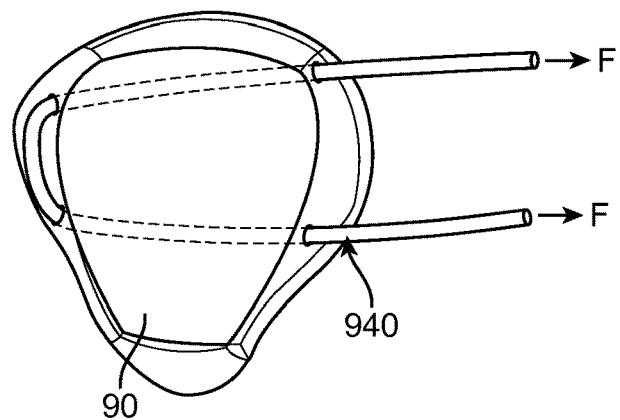
FIG. 21 is a front view of another tensioning implant.
Figure 22:
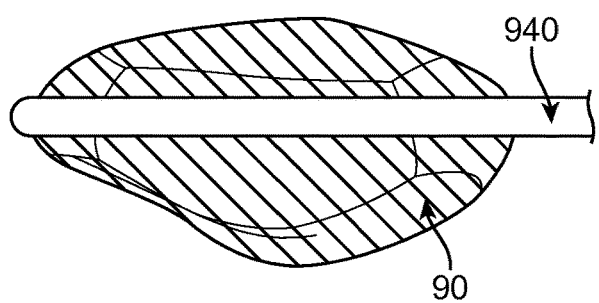
FIG. 22 is a cross sectional view of the implant of FIG. 21.

FIGS. 21 and 22 illustrate another tension implant 940 in the form of a tension band which is secured to the patella by forming one or more tunnels thorough the patella and threading the tension band through the tunnels. The tension bands or tension elements described herein with respect to FIGS. 21 and 22 and the other embodiments of the invention can be shaped as a tubular element such as a cord or suture. The tension bands may be made of a material that is elastic, rigid or semi-rigid. The band can be woven, circular, a flat band or other shape. In the embodiment of FIGS. 21 and 22, the two tunnels are formed though the patella from the medial to the lateral side of the patella and the tension implant 940 is threaded though both tunnels with the ends of the band secured to the femur, tibia or fibula to apply an aligning force F to the patella.

Figure 23:
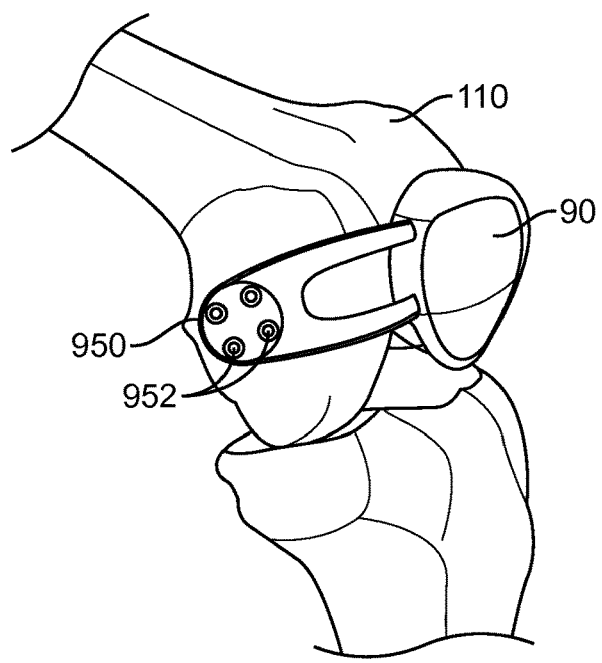
FIG. 23 is a perspective view of another tensioning implant.

FIG. 23 shows one embodiment of a femoral securing base 950 for securing one of the tension elements described herein, such as the tension implant 940, to the femur 110. In this example the femoral base 950 is secured to the femur by four screws 952, however, other numbers of screws may be used.

FIGS. 24 and 25 illustrate a tension implant 960 including a thin plate 962, a plurality of bone screws 964, and a tension band 966. The thin plate 962 has a hook shaped portion 968 formed at one side of the patella which is configured to form a tunnel to receive the tension band 966. The tension member 966 loops through the tunnel and is secured at the other end by a plate, screw or other fastener to the femur, tibia or fibula.

FIGS. 26 and 27 show a tension implant 980 which shifts the load on the patella with a wedge shaped implant 980 which lifts the medial patella-femoral ligament 984. The wedge shaped implant 980 is secured to the femur by bone screws or other fastening means. The wedge 980 lifts and tightens the medial patella-femoral ligament and shifts the patella 90 in the medial direction as shown in FIG. 27 to alter the tracking of the patella by using the increase in tension in the joint's own anatomy. Alternatively, by placing the implant 980 on the lateral side of the patella, a lateral shift of the load on the patella is obtained.

Figure 28:
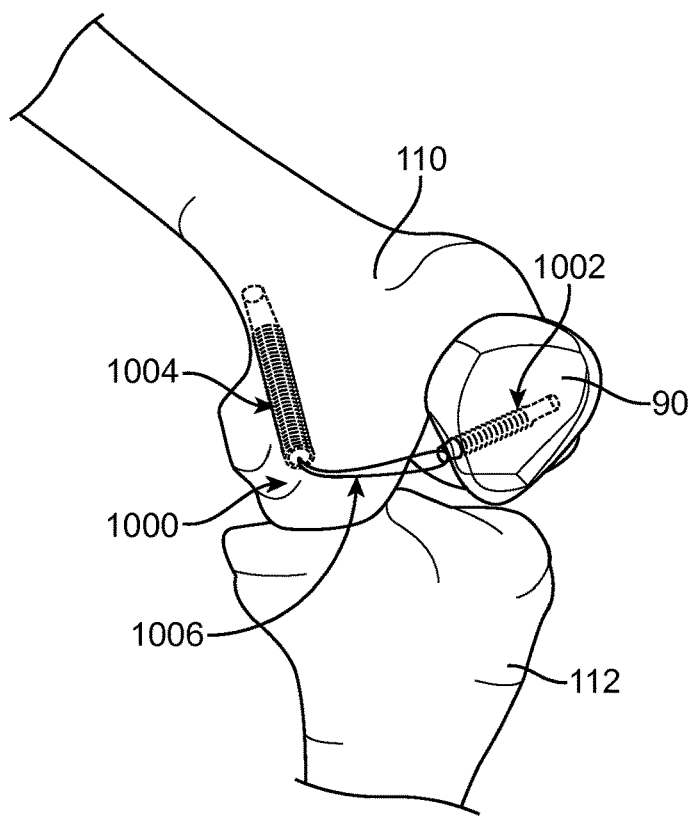
FIG. 28 is a perspective view of a spring anchor tensioner implant implanted on a knee joint.
Figure 29:
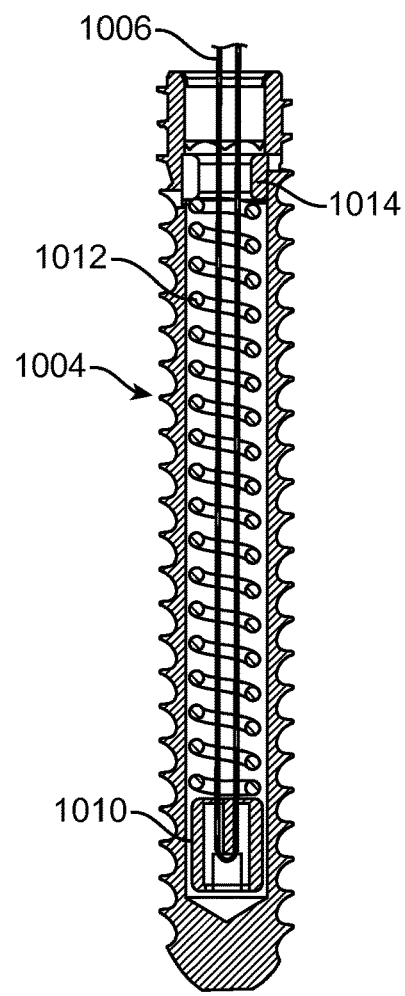
FIG. 29 is a cross sectional view of the spring anchor.
Figure 30:
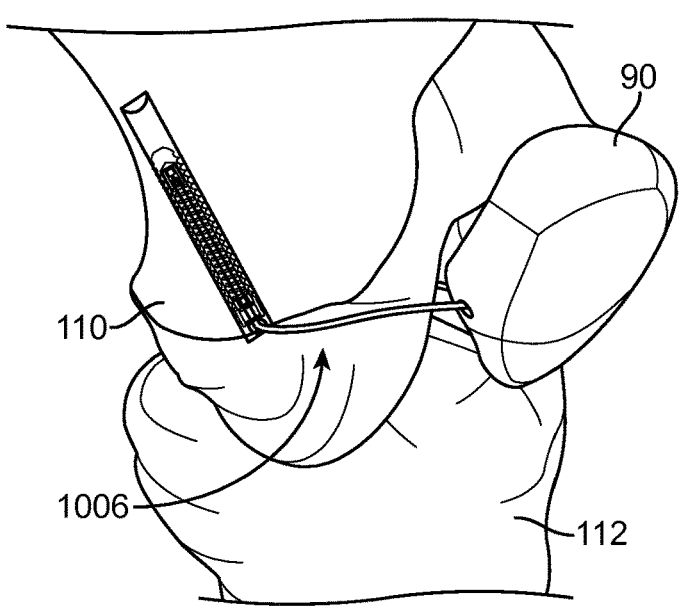
FIG. 30 is a perspective view of the spring anchor tensioner of FIG. 28.

FIGS. 28-30 relate to a patella tension implant 1000 including a spring loaded piston. The implant 1000 includes a suture anchor 1002 secured in the patella 90, a spring anchor tensioner 1004 secured in the femur 1112 and a suture 1006 therebetween. One example of a spring anchor tensioner 1004, shown in FIG. 29, is inserted by threading into the femur. The suture anchor 1002 can be any one of the known suture anchors, such as threaded anchors having attachments such as eyelets for attaching suture to the head of the anchor. The tensioner 1004 includes threaded body having in hollow interior and a spring loaded piston 1010 and spring 1012 inside the tensioner. As shown in FIG. 29, the spring 1012 is positioned between the piston 1010 and a shoulder or retainer 1014. The retainer 1014 may be fixed or movable, such as by threads or a ratchet mechanism to adjust the pre-load on the spring. The suture 1006 may pass through or around the spring 1012 and attached to the piston

1010. The spring 1012 can be pretensioned in the tensioner. Although the patella tension implant 1000 is shown as having the tensioner 1004 implanted in the patella, the tensioner may also be located inside or along the side of other bones of the joint including the patella, tibia and fibula.

The patella tension implant 1000 can be implanted by forming an incision at the knee joint and predrilling holes in the patella and femur to receive the suture anchor 1002 and the tensioner 1004. The tensioner 1004 with the suture attached is then inserted into the hole in the femur. A tissue tunnel is formed through the subcutaneous tissue and the suture 1006 is threaded from the tensioner 1004 to the location where the suture anchor 1002 is secured to the patella. The suture 106 is then threaded through the suture anchor 1002 and secured by tying or other means. Once the suture 1006 is attached, the spring 1012 will act to allow the suture to extend as the joint articulates while providing the desired tension on the patella.

Figure 31:
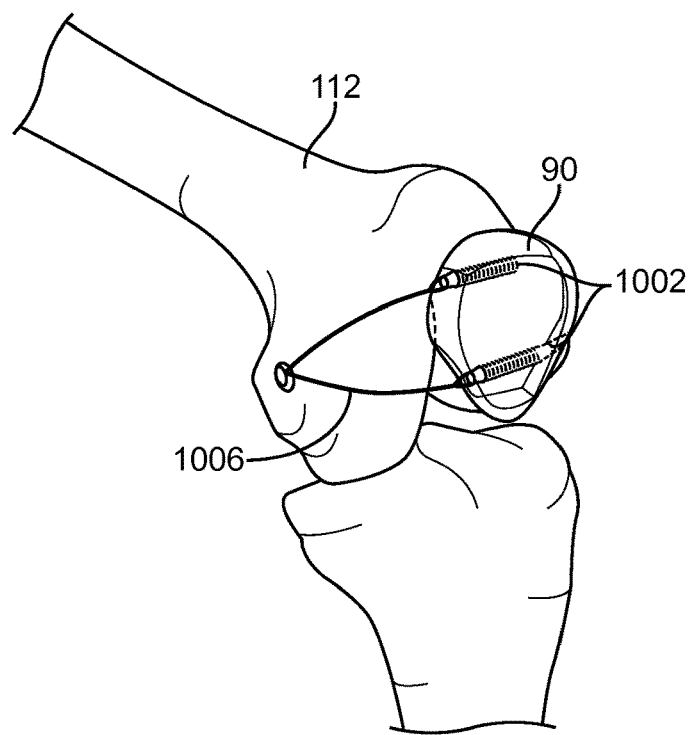
FIG. 31 is a perspective view of another configuration of a spring anchor tensioner on a knee joint.
Figure 32:
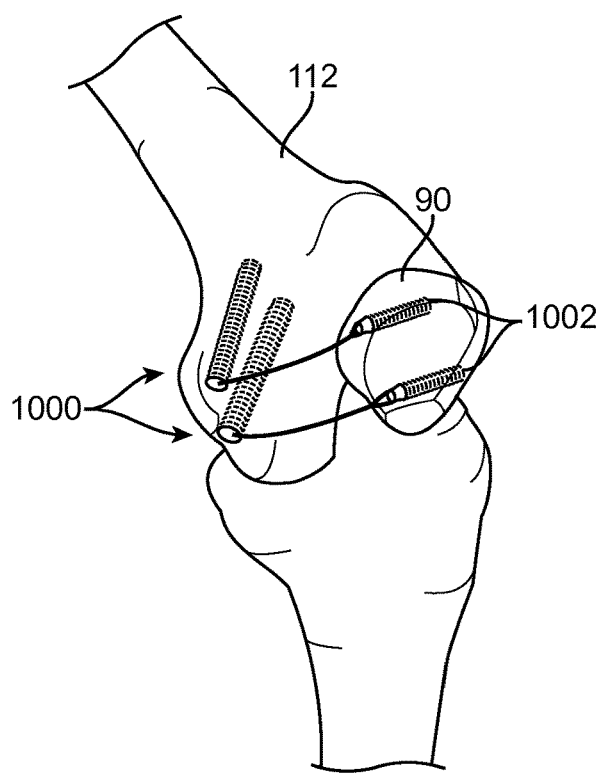
FIG. 32 is a perspective view of a knee joint with two spring anchor tensioners.
Figure 33:
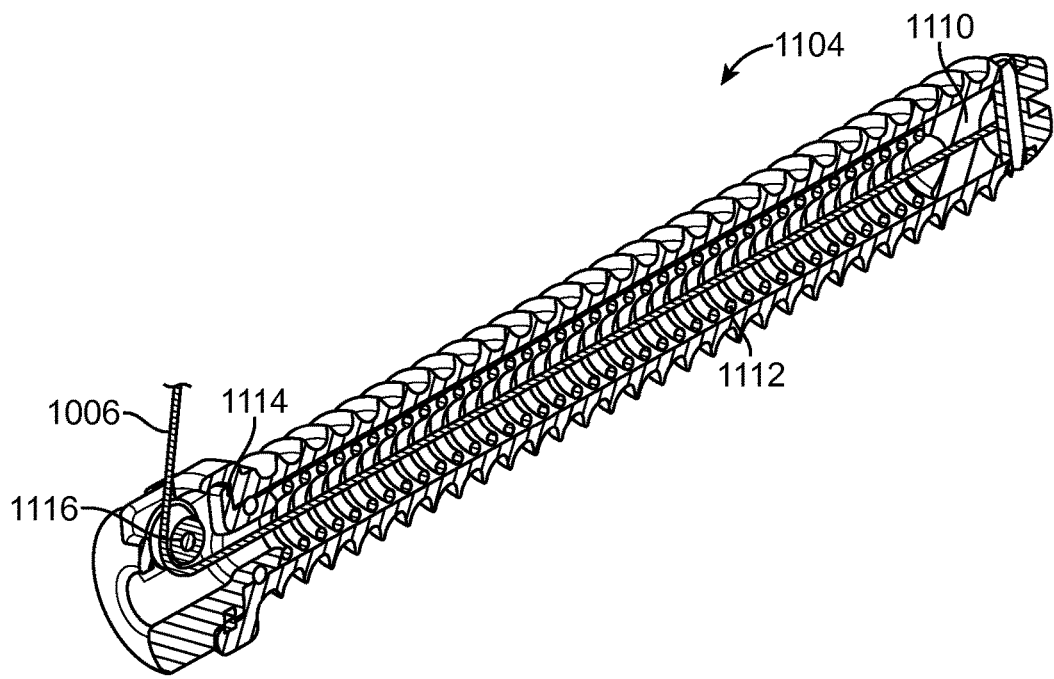
FIG. 33 is a cross sectional view of another spring anchor.

Different numbers and positions of the suture anchor 1002 and tensioner 1004 may be used depending on the treatment to be achieved. FIGS. 31-33 illustrate other variations on the use of the patella tension implant 1000. Some of the several working arrangements that can be used to address specific lesions of the patella/femoral cartilage surface include:
a) a single spring-anchor inserted in the femur, near its distal end, an anchor secured to the patella and a tension member tensioning between the two (FIGS. 28 and 30);
b) a spring anchor fixated to the patella; the rigid anchor secured to the femur and a tension member tensioning between the two (not shown);
c) two spring anchors used; one anchor is fixated to the femur and the second to the patella, the tension member is tensioned between the two (not shown);
d) two spring anchors inserted in the patella and a spring tensioner is implanted in the femur (FIG. 31);
e) two or more entire tensioner implant systems implanted between the patella and femur with the same or different tension forces applied by each system to achieve tension in two different directions or at different flexion angles (FIG. 32).

The suture 1006 may be rigid or may be elastic. Each individual tensioner 1004 may have a different spring rate. Alternately, a single tensioner may be provided with multiple springs to provide different tension to more than one suture.

FIG. 33 is a cross sectional view of another spring anchor tensioner 1104 including a threaded body having in hollow interior and a spring loaded piston 1110 and spring 1112 inside the tensioner. As shown in FIG. 33, the spring 1112 is positioned between the piston 1110 and a shoulder or retainer 1114. The retainer 1114 may be snapped or screwed into place in the tensioner and may include a pulley 1116 for changing the direction of the suture 1006 while minimizing damage or wear to either the suture of the tensioner. The spring 1112 can be a compression spring as shown in FIG. 33 and may be pretensioned in the tensioner.

Figure 34:
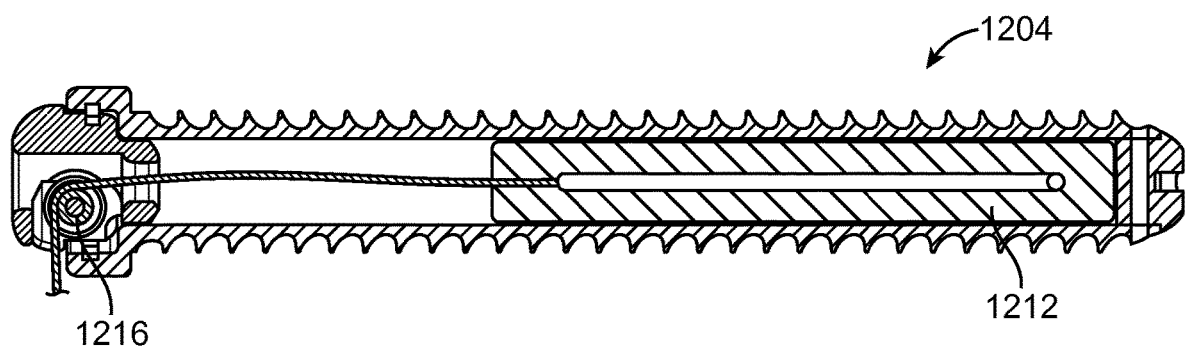
FIG. 34 is a cross sectional view of an additional spring anchor.

FIG. 34 shows an alternate version of a spring anchor tensioner 1204 having tension spring element in the form of an elastomeric material. In the spring anchor tensioner 1204, an elastomeric spring 1212 which is shown in the form of a slotted cylinder is provided inside the threaded body of the tensioner 1204 and secured to the distal end of the body. As in FIG. 33, the tensioner 1204 can be provided with a proximal end pulley 1216 for assisting in the transition of the suture around a bend of anywhere from about 60-130 degrees.

FIGS. 35-41 illustrate tensioning implants formed of molded elastic or elastomeric material, such as those shown and described above in connection with the embodiments of FIGS. 9-15. The tensioning implant 2000 of FIGS. 35-41 includes a molded elastomeric member 2002 which provides tensioning and is connected at a femoral end to a pin 2004 and at a patella end is provided with a channel 2006 for receiving a fastener. In the version shown in FIG. 36, the elastomeric member 2002 is overmolded onto a head of the pin 2004 between two annular flanges 2008. A threaded bone screw 2010 has a central channel configured to receive the shaft of the pin 2004 in a freely rotatable manner. The inner one of the annular flanges 2008 provides a bearing surface for rotation of the pin 2004 within the bone screw 2010. The bone screw 2010 is provided with a feature, such as a hex feature either at the top surface or within the central channel for receiving a driver.

Figure 37:
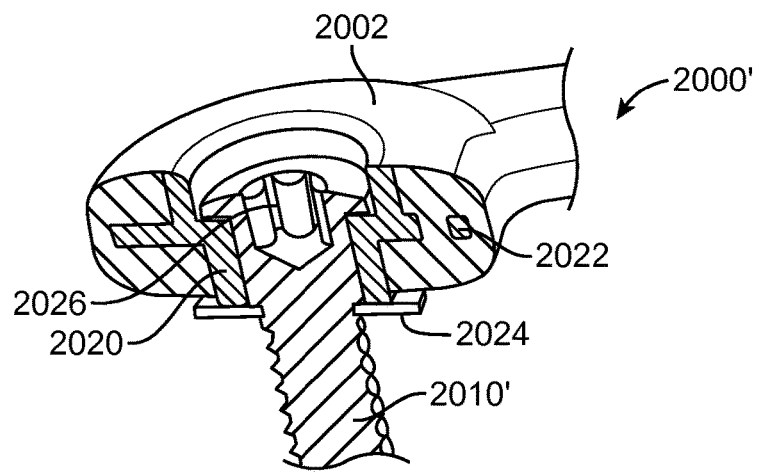
FIG. 37 is a cross sectional perspective view of an alternative attachment for the tensioning implant of FIG. 34.

FIG. 37 illustrates an alternative embodiment of a tensioning implant 2000' in which the elastomeric member 2002 is overmolded onto a pivoting anchor head 2020 which may include a perforated annular rim 2022 for improved connection. The anchor head 2020 is mounted around and pivots on the bone screw 2010'. The bone screw 2010' may be provided with an rigid annular flange 2024 which serves as a bearing surface of the anchor head 2020. The bone screw 2010' is also provided with an internal feature 2026 for receiving a driver.

Figures 35, 36:
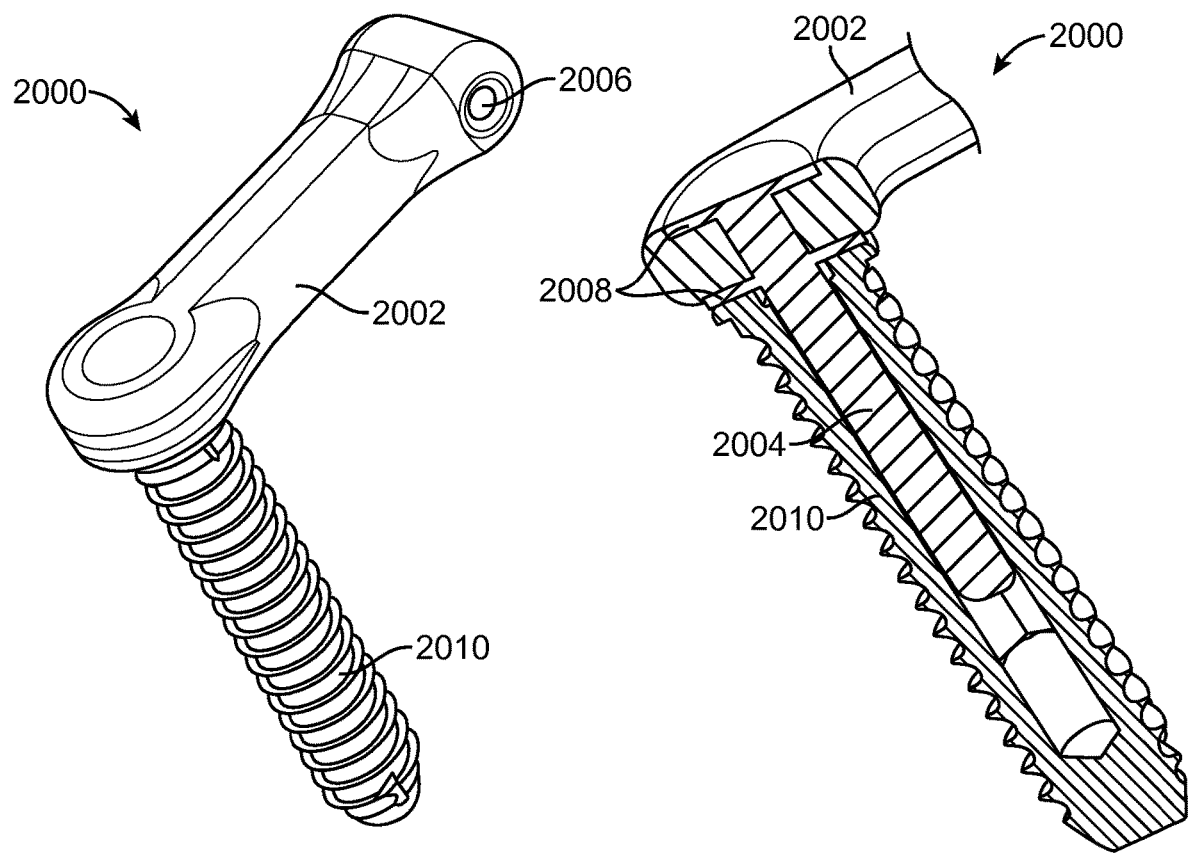
FIG. 35 is a perspective view of a tensioning implant.
FIG. 36 is a cross sectional perspective view of the tensioning implant of FIG. 35.
Figure 38:
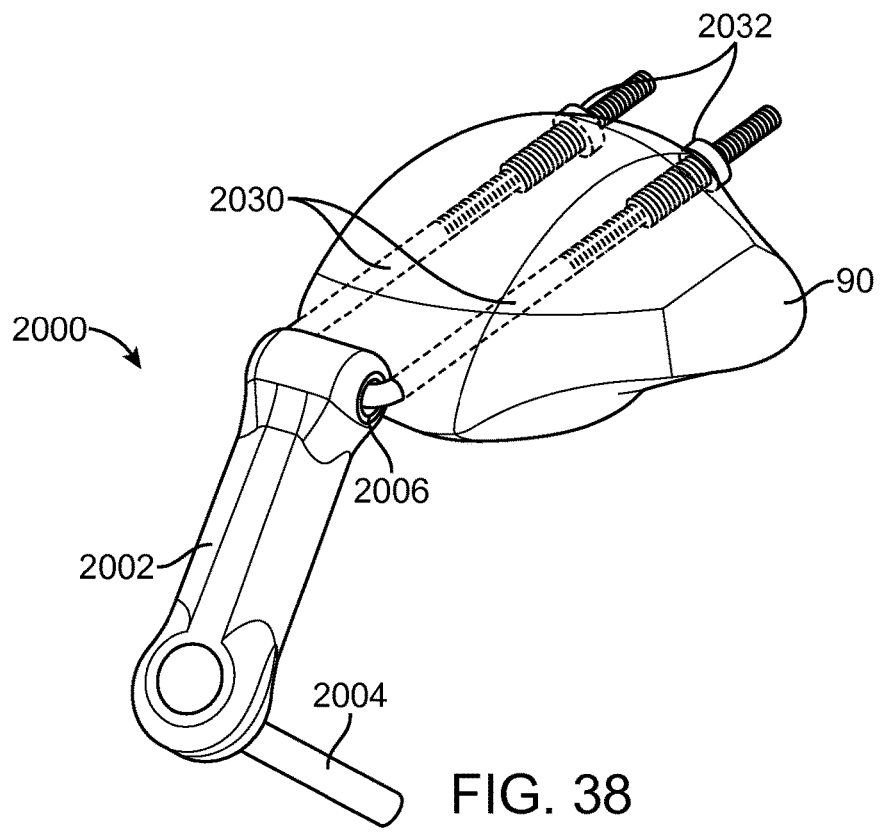
FIG. 38 is a perspective view of a tensioning implant attached to a patella.

The channel 2006 shown in FIG. 35 can be used to connect the tensioning implant to the patella in a variety of manners shown in FIGS. 38-41. In the embodiment of FIG. 38, a rigid bolt or wire structure extends through the channel 2006 with the two shafts of the bolt structure 2030 extending through the patella and two nuts 2032 fastened to the shafts on an opposite side. A similar structure may also be formed from flexible material such as a suture which can extend through the channel 2006 and connect to the patella. In the case of a flexible connecting structure, such as suture, it may be desirable to place a rigid tube within the channel 2006.

Figures 39, 40:
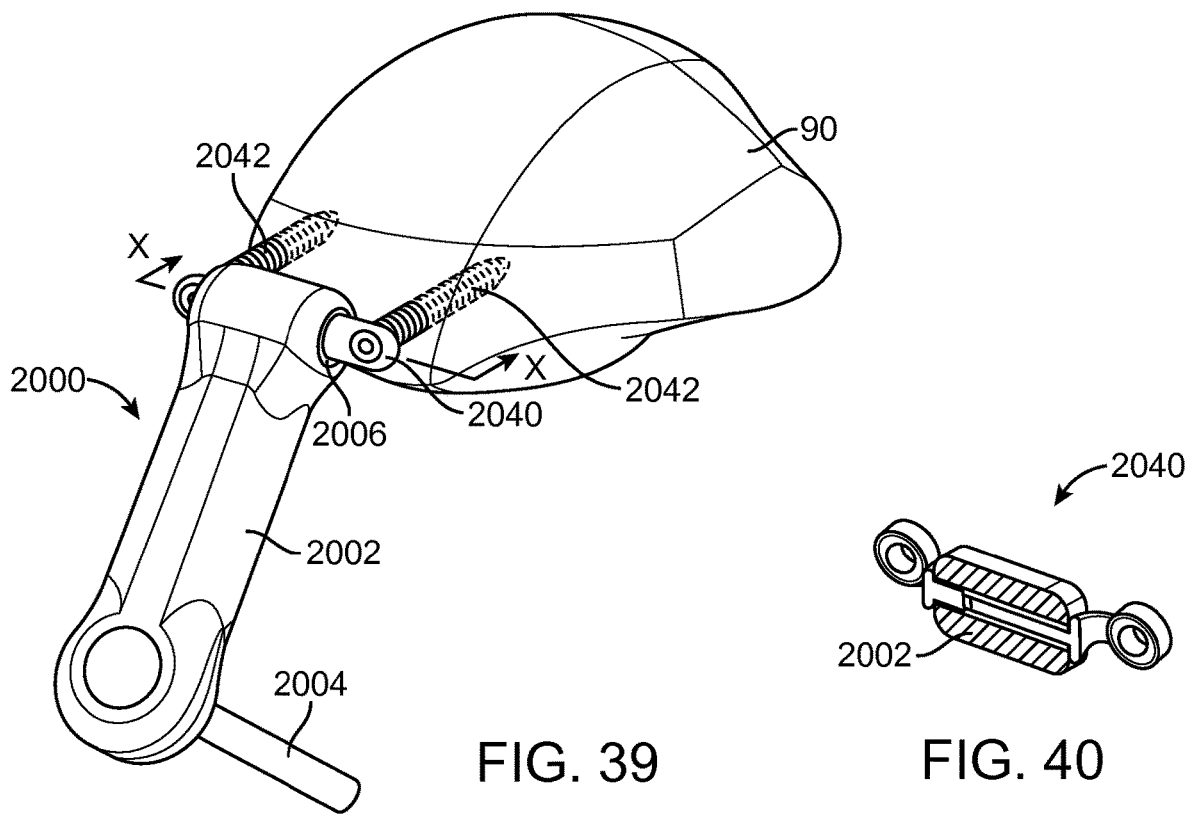
FIG. 39 is a perspective view of the tensioning implant of FIG. 38 attached to a patella in a different manner.
FIG. 40 is a cross sectional perspective view the tension implant of FIG. 39 taken along line X-X.

FIGS. 39 and 40 show a traverse bearing 2040 extending through the channel 2006 and connected to the patella with bone screws 2042. In each of the embodiments of the tensioning implants 2000 and 2000', the patella end of the implant provides one degree of rotational freedom and possibly some lateral translation of the elastomeric member 2002 with respect to the bolt, wire or bearing member 2040. Meanwhile, the femoral end of the implants 2000 and 2000' provide one degree of rotational freedom about the pin 2004 in a direction which is substantially perpendicular to the rotational motion at the patella end.

Figure 41:
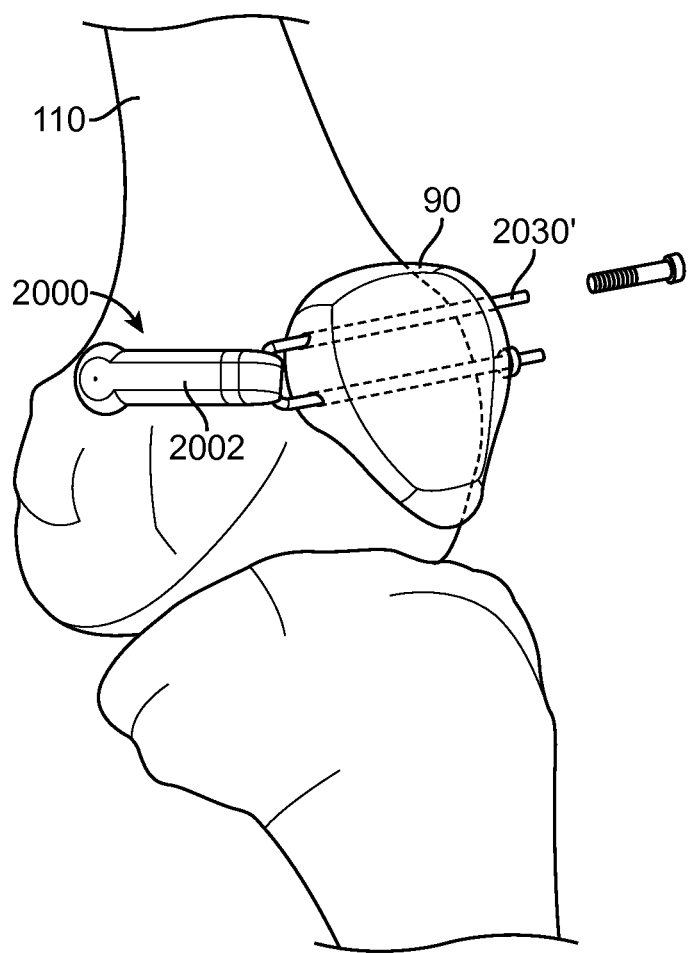
FIG. 41 is a perspective view of another tension implant system.

FIG. 41 illustrates the attachment of a tensioning implant 2000 to the patella 90 and the femur 110.

Conventional approaches to inserting the above-described implants within knee anatomy are contemplated. Arthroscopic approaches can be employed along with fluoroscopy or other imaging techniques to properly position the treatment devices. Prior to implantation, the anatomy of the patient's knee is accessed to determine a best course of treatment, and to identify a configuration of implant which best suits the patient's specific condition. The knee is rotated and turned through its full range of motion to identify proper implantation sites and to access the tracking pattern of the patella. The surgeon selects an implant configuration that will function in the best manner for redistributing tensions and contact forces, with the objective of reducing pain and correcting the tracking pattern of a patella. Further, the implant is configured to correct the tracking pattern of the patella through a full range of motion of the knee joint or throughout normal gait. Subsequent to implantation, the implant can be reconfigured to present an altered profile to achieve optimum results. The implant can be used to both shift and rotate the patella to provide correct patella tracking.

In some cases, the patella tracking correction implants described herein may be used in combination with treatment called a lateral release. The lateral release is used to further improve tracing of the patella. It is generally performed arthroscopically and involves cutting through a portion of the lateral retinaculum to release some of the lateral tension on the patella and allow the patella to return to a more normal tracking pattern with the assistance of the implant.

The foregoing therefore provides an implant embodying a structure ensuring proper tracking of the patella during the entire gait cycle. The size or stiffness of the implant can be altered to achieve the desired tracking. In the event multiple tensioning bands are employed, they may be parallel, non-parallel, or crossing to achieve the desired tracking.

Thus, it will be apparent from the foregoing that, while particular forms of the invention have been illustrated and described, various modifications can be made without parting from the spirit and scope of the invention. In particular, one or more features of one specific approach can be incorporated into another approach. Additionally, the present disclosure can be made to be applicable to other medical conditions.

We claim:

1. A patella shifting implant useful for positioning between a patella and a femur of a patient, the implant comprising:
   a first attachment member for attaching a first end of the implant to the patella, the first attachment member comprising a rigid bone anchor;
   a second attachment member for attaching a second end of the implant to the femur, the second attachment member comprising a rigid bone anchor;
   an elastomeric tensile member extending between the first attachment member and the second attachment member and configured to alter a tracking pattern of the patella when the implant is implanted thereon;
   at least one rotatable coupling;
   wherein the tensile member is connected to at least one of the first and second attachment members by said at least one rotatable coupling to permit the tensile member to rotate relative to said at least one of the first and second attachment members; and
   wherein said at least one rotatable coupling comprises a snap lock connector secured to the tensile member and to the rigid bone anchor.

2. The implant of claim 1, wherein the tensile member is Y-shaped including first and second legs having separated free ends and a common end.

3. The implant of claim 2, further comprising:
   a third attachment member for attaching said first end of the implant to the patella;
   wherein the first and third attachment members are secured to said separated free ends of said first and second legs; and
   wherein said second attachment member is secured to said common end of said first and second legs.

4. The implant of claim 1, wherein the snap lock connector comprises a plurality of prongs and the rigid bone anchor comprises an interior cavity including a snap lock feature sized to receive said prongs therein so that the prongs secure the tensile member to the rigid bone anchor and are rotatable relative to the rigid bone anchor.

* * * * *